United States Patent [19]
Kuwabara et al.

[11] Patent Number: 5,408,512
[45] Date of Patent: Apr. 18, 1995

[54] LOCAL ANALYSIS OF A SPECIMEN IN AN X-RAY FLUORESCENCE SPECTROMETER

[75] Inventors: Shoji Kuwabara, Osaka; Masakazu Yoshioka, Shiga; Tatsuru Ito, Kyoto, all of Japan

[73] Assignee: Shimadzu Corporation, Kyoto, Japan

[21] Appl. No.: 153,335

[22] Filed: Nov. 16, 1993

[30] Foreign Application Priority Data

Apr. 23, 1993 [JP] Japan .................................. 5-097744
May 12, 1993 [JP] Japan .............................. 5-024520 U

[51] Int. Cl.⁶ .......................................... G01N 23/223
[52] U.S. Cl. ........................................ 378/45; 378/49; 378/148
[58] Field of Search ................ 378/45, 44, 48, 49, 378/50, 147, 148, 149, 150, 152

[56] References Cited

U.S. PATENT DOCUMENTS

| | | | |
|---|---|---|---|
| 3,075,079 | 1/1963 | Tabikh | 378/49 |
| 4,417,355 | 11/1983 | Anisovich et al. | 378/49 |
| 4,562,585 | 12/1985 | Göbel et al. | 378/49 X |

FOREIGN PATENT DOCUMENTS 0027695  3/1977  Japan .................................. 378/148

Primary Examiner—David P. Porta
Attorney, Agent, or Firm—Heller, Ehrman, White & McAuliffe

[57] ABSTRACT

An X-ray fluorescent spectrometer uses a screen which restricts a field of view to a local portion of a specimen irradiated by X-rays from an X-ray tube. Fluorescent X-rays from the specimen from the local portion and passing through the screen are collimated, dispersed and analyzed. A control unit controls a rotating mechanism to rotate the specimen or its container around a predetermined axis and also a moving mechanism to linearly move the screen such that the local portion to be analyzed and a throughhole of a proper size therefor can be brought adjacent each other. Data on the positions of local portions to be analyzed on the specimen can be inputted through an input unit. Effects of variations in detection results due to different distances between the analyzed local portions and the axis of rotation can be compensated for by storing reference data obtained from a standard sample in a data processing unit.

9 Claims, 11 Drawing Sheets

LOCAL ANALYSIS OF A SPECIMEN IN AN X-RAY FLUORESCENCE SPECTROMETER

BACKGROUND OF THE INVENTION

1. Field of the Invention

This invention relates to an X-ray fluorescence spectrometer using a beam-collimating method and, more particularly, to an X-ray fluorescence spectrometer suited for local analyses of a specimen.

2. Description of Related Art

As shown in FIG. 10, an X-ray fluorescence spectrometer using a beam-collimating method contains a specimen 2 inside a specimen container 8. Only a selected portion of the surface of the specimen 2 at the center of the container 8 is exposed to the exterior of the container 8 for local analyses. As the primary X-rays from an X-ray tube 1 irradiate the specimen 2 thus disposed, fluorescent X-rays are generated at a local portion of the specimen 2 and are guided through a view-restricting screen 3 to primary Soller slits 4. The Soller slits 4 serve to collimate the fluorescent X-rays and to guide them to an analyzing plate crystal 5, which disperses the incident fluorescent X-rays into a spectrum of different wavelengths corresponding to the elements contained in the specimen 2. The dispersed beam is thereafter led to secondary Soller slits 6, collimated thereby and received by an X-ray detector 7 for detecting the elements in the local portion of the specimen 2 from the detected spectrum.

With an arrangement as described above, it is difficult to have only the specimen 2 irradiated with the primary X-rays from the X-ray tube 1 because a part of the primary X-rays is likely to irradiate the container 8. As a result, the irradiation by the primary X-rays may cause not only the generation of fluorescent X-rays from the local portion intended to be analyzed, but also the generation of fluorescent and scattered X-rays from the container 8. If such fluorescent and scattered X-rays from the container 8 are additionally received by the X-ray detector 7 through the Soller slits 4 and 6 as described above, they create a background against the spectrum of the fluorescent X-rays of interest for the analysis of the elements in the local portion of the specimen 2. In other words, the signal-to-noise ratio (S/N) of the X-ray detector 7 is adversely affected. This is why the view-restricting screen 3 is interposed between the specimen 2 and the primary Soller slits 4 to limit the field of view from the primary Soller slits 4 to the local portion of the specimen 2.

As shown more clearly in FIG. 11, the specimen 2 is retained in the container 8 with its peripheral portion covered such that only its local portion at the center is externally exposed. The view-restricting screen 3 is composed of a flat plate 3a having a plurality of holes (such as three holes 3b, 3c and 3d) each corresponding to the size of different one of the local portions to be analyzed. In situations where local portions with different sizes are to be analyzed, the screen 3 is slid in the direction indicated by an arrow A such that a hole of an appropriate size will be positioned at the center of the container 8.

If the local portions to be analyzed are at different positions but are of the same size, the screen 3 need not be moved, but the specimen 2 is moved from one position to another such that each local portion to be analyzed will come to the center position of the container 8. Depending on the shape and/or size of the specimen 2 with respect to the container 8, however, it may be difficult to place certain local portions precisely at the center as required. In such a situation, it may be necessary to subdivide the specimen 2 into smaller parts. It now goes without saying that such a process makes the analysis very troublesome.

When the exposed area of the specimen 2 is increased, or when the local portions to be analyzed are large, the distance by which the specimen 2 or the container 8 must be moved becomes also large. Depending on how various internal components of the spectrometer, such as the X-ray tube 1, are arranged, there may not be enough room to move the container 8 as required. If it is attempted to secure enough space for maneuvering the container 8, this may have an adverse effect on the detection sensitivity of the X-ray detector 7.

SUMMARY OF THE INVENTION

Accordingly, it is an object of the invention to provide an improved X-ray fluorescence spectrometer capable of facilitating the analysis of different local portions of a specimen.

It is another object of the invention to provide an improved X-ray fluorescence spectrometer with which different local portions of a specimen can be analyzed without moving the specimen or its container such that the detection sensitivity of its X-ray detector is not adversely affected.

Other objects of the invention will become apparent from the description given below, but it should be understood that the description and examples given below are intended to illustrate the invention, and not to limit the scope of the invention, since many modifications and variations of the examples disclosed herein are within the scope of the invention.

An X-ray fluorescence spectrometer according to a preferred embodiment of the invention, with which the above and other objects can be achieved, may be characterized as comprising a view-restricting screen for restricting the field of view to local portions of a specimen irradiated by X-rays from an X-ray tube, primary Soller slits for collimating fluorescent X-rays received from the specimen through the screen, moving means for moving the screen linearly by a distance within a predetermined range in a direction perpendicular to the incident optical axis of the primary Soller slits, and control means for controlling the moving means such that the screen may be opposite a local portion of the specimen. Preferably, a rotating means may also be included for rotating the specimen around a predetermined axis of rotation, controlled also by the control means.

The view-restricting screen, according to a preferred embodiment of the invention, is formed with a plurality of holes, each with an aperture of a different size, and a hollow (or tubular) frustoconical member is mounted around each of these holes.

According to still another preferred embodiment of the invention, there is a mark attached to the specimen container on its side, serving as a reference point when the container is rotated. A mark-detecting means is also provided for detecting the mark and outputting a signal indicative of its angular position.

With an X-ray fluorescence spectrometer thus structured according to the invention, a specimen can be rotated and the screen can be moved by any distance within predetermined ranges. Thus, although a local portion to be analyzed is minute and at a position significantly removed from the center of the specimen, it can be moved to a position adjacent the screen.

BRIEF DESCRIPTION OF THE DRAWINGS

The accompanying drawings, which are incorporated in and form a part of this specification, illustrate embodiments of the invention and, together with the description, serve to explain the principles of the invention. In the drawings.

In all these figures, like components are indicated by the same numerals.

DETAILED DESCRIPTION OF THE INVENTION

The invention will be described with reference to the drawings.

Figure 1:
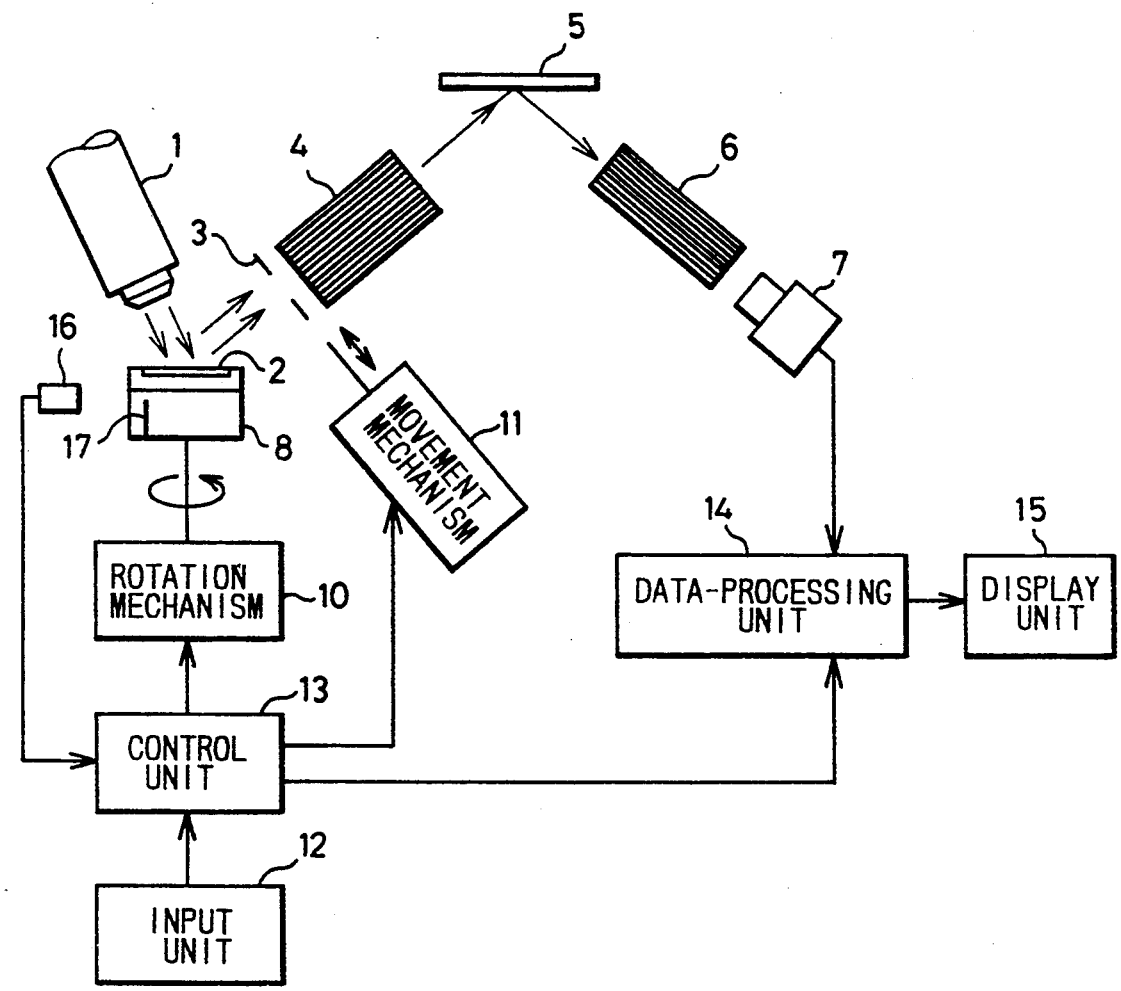
FIG. 1 is a schematic, in part in the form of a block diagram, of an X-ray fluorescence spectrometer according to a first embodiment of the invention.
Figure 2:
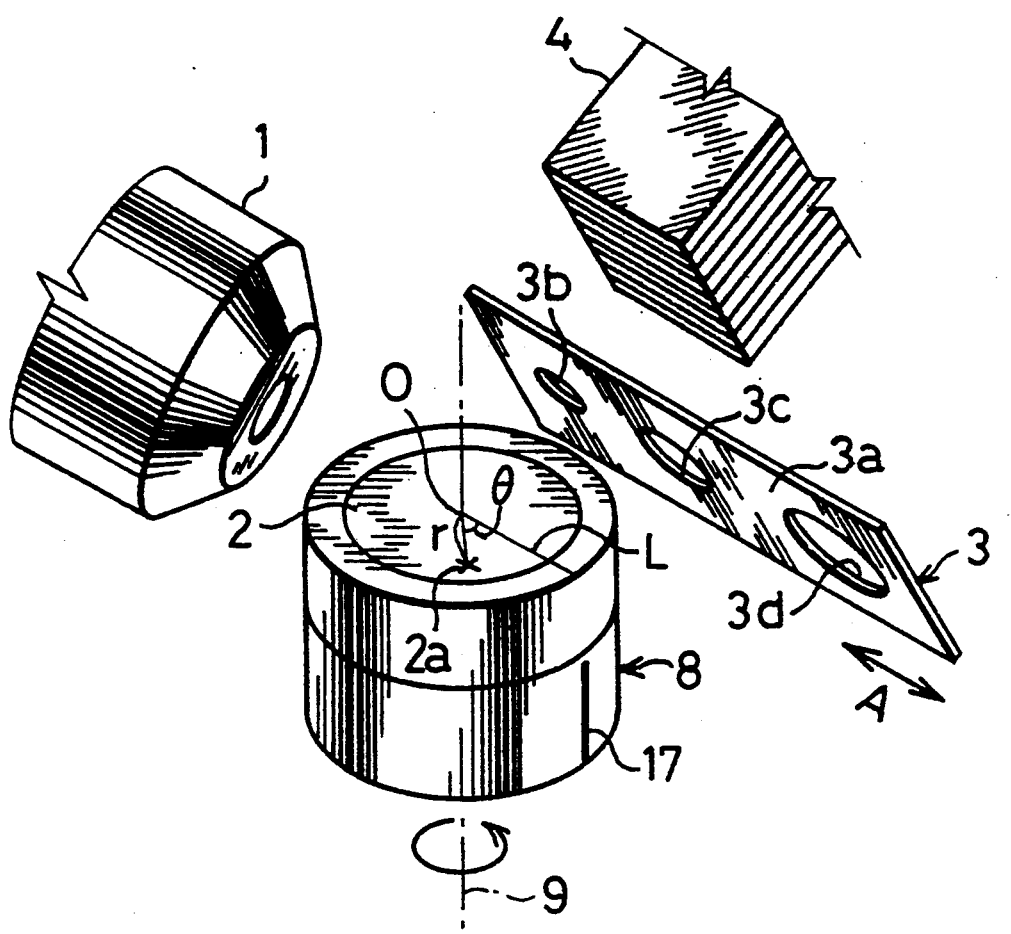
FIG. 2 is an enlarged perspective view of a portion of the spectrometer of FIG. 1.
Figure 10:
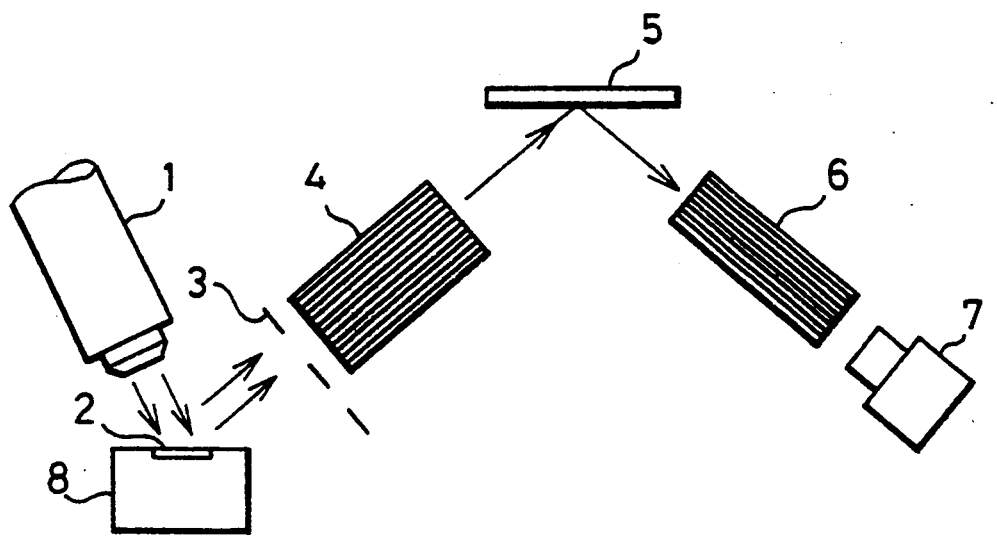
FIG. 10 is a schematic of a conventional X-ray fluorescence spectrometer.
Figure 11:
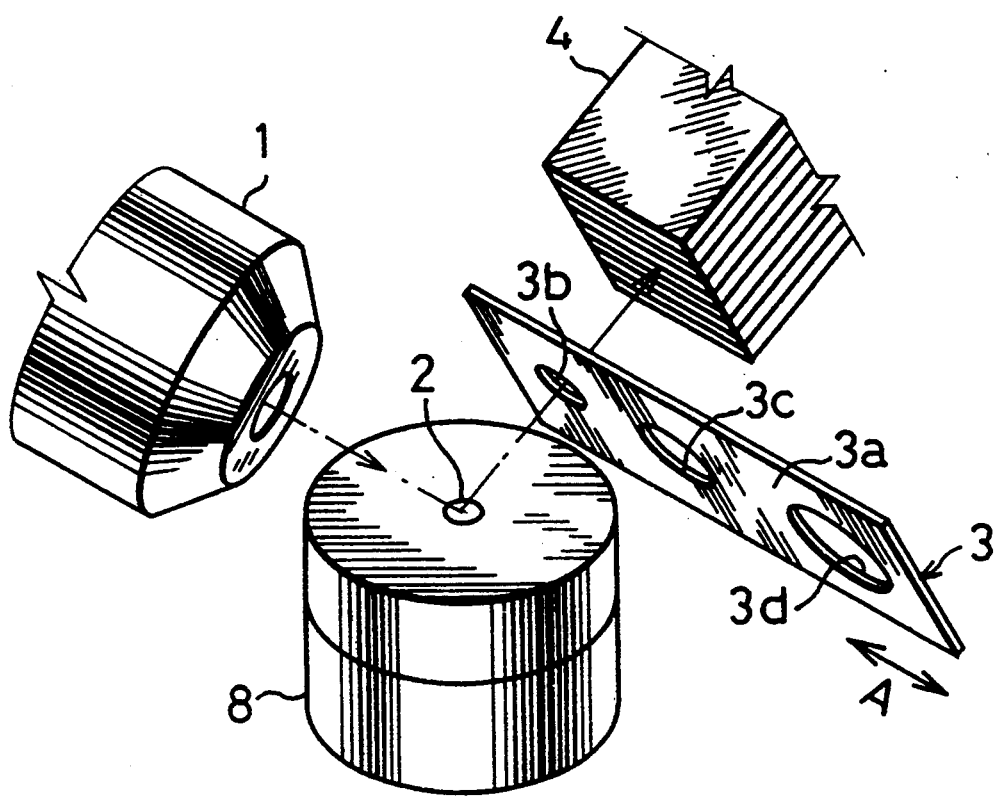
FIG. 11 is a perspective view of a portion of the spectrometer of FIG. 10.

An X-ray fluorescence spectrometer according to a first embodiment of the invention comprises, as shown in FIGS. 1 and 2, an X-ray tube 1, a specimen container 8, a view-restricting screen 3, primary Soller slits 4, an analyzing plate crystal 5, secondary Soller slits 6, and an X-ray detector 7. The basic functions of these components are substantially the same as explained above with reference to FIG. 10.

For facilitating the analysis of any local portion at an off-center position of a specimen 2, the spectrometer further comprises a rotation mechanism 10 such as a pulse motor for rotating the container 8 by any angle around a predetermined axis of rotation, a movement mechanism 11 including a motor, a gear and the like for moving the screen 3 linearly by any distance within a certain range in a direction indicated by arrow A perpendicular to the optical axis of the primary Soller slits 4 on the incident side thereof, and an input unit 12 such as a keyboard through which the position of each of the local portions to be analyzed can be specified.

A control unit 13, a data processing unit 14 and a display unit 15 may be further provided. The control unit 13 is for controlling the rotation and movement mechanisms 10 and 11 such that the screen 3 can be brought to a position in a face-to-face relationship with a specified local portion of the specimen 2. The data processing unit 14 serves to make sensitivity corrections if the local portion being analyzed has slipped off the center of the specimen 2 and also to carry out various analyses and processes. The display unit 15 may comprise a cathode-ray tube (CRT) for displaying results of the analysis.

The area of the specimen 2 exposed externally from the container 8 may be greater than in the case of conventional spectrometers. Let us consider a situation, as shown in FIG. 1, where a rather small portion of that relatively large exposed area is selected as a local portion 2a to be analyzed. As explained above, the specimen container 8 of FIGS. 1 and 2 can be rotated by means of a pulse motor (serving as the rotation mechanism 10). A mark 17 is provided on the container 8 to indicate its angular position, and a mark-detecting unit 16 such as a photosensor is positioned near the container 8. The view-restricting screen 3 comprises a flat plate 3a having three holes 3b, 3c and 3d of different sizes corresponding to the sizes of the local portions intended to be analyzed.

The movement mechanism 11 moves the screen 3 in a direction perpendicular to the optical axis of the Soller slits 4 on its incident side as indicated by arrow A in FIG. 2 such that the holes 3b, 3c and 3d can selectively come to a position opposite the center part of the container 8. Thus, even if a local portion of the specimen 2 is at an off-center position, the movement mechanism 11 can move the screen 3 such that one of the holes 3b, 3c or 3d comes to a position adjacent to such an off-center local portion to be analyzed As explained above briefly, the input unit 12 allows position data to be inputted for defining the positions of local portions to be analyzed. Such position data may include the distance r of the local portion from the center (or the center of rotation) O of the container 8 and its angle $\theta$ from the angular position of the mark 17 used as the reference. The control unit 13 controls the rotation and movement mechanisms 10 and 11 on the basis of the values of r and $\theta$ inputted from the input unit 12. In the case of a very small local portion, for example, the smallest of the three holes 3b, 3c and 3d (3b in the illustrated example) corresponding to the size of the local portion 2a is brought opposite thereto according to the position data inputted through the input unit 12. In other words, as these position data are inputted through the input unit 12, the control unit 13 causes the container 8 to be rotated by controlling the rotation mechanism 10 until the photosensor 16 outputs a detection signal to the control unit 13 upon detecting the mark 17 to first ascertain the reference angular direction. The control unit 13 then causes the container 8 to further rotated by $\theta$ such that the local portion 2a of interest lies on a straight line L passing through the center (of rotation) O of the container 8 and lying parallel to the direction of the linear motion of the screen 3.

Next, the control unit 13 causes the movement mechanism 11 to move the screen 3 in the direction of arrow A, parallel to the line L such that the smallest hole 2b, matching in size with the selected local portion at a distance r from the center O, comes to a position opposite thereto.

For an analysis, the specimen 2 is irradiated by the primary X-rays from the X-ray tube 1. As a result, fluorescent X-rays are generated at the local portion 2a of interest, and these rays are introduced through the screen 3 into the primary Soller slits 4 and thereby collimated. The fluorescent X-rays, thus collimated, are dispersed into a spectrum of wavelengths by the analyzing plate crystal 5 and then detected through the secondary Soller slits 6 by the X-ray detector 7. Detection outputs from the X-ray detector 7 are transmitted to the data processing unit 14.

Since the distance r changes, from one selected local portion to another, the detection sensitivity of the X-ray detector 7 also varies, depending on the value of r corresponding to each local portion. The data processing unit 14 is adapted to correct this variation in the detection sensitivity. For this purpose, a copper plate, for example, may be used as a standard specimen having preselected homogeneous compositions. After such a standard specimen is properly set in the container 8, an output from the X-ray detector 7 is measured at each of local portions at different distances r from the center of rotation of the container 8. In this manner, the variation in the detection sensitivity of the X-ray detector 7 depending on the distance r becomes known, and this preliminarily determined variation in the detection sensitivity is stored in the data processing unit 14 as correction data to be used for compensating for the changes in the sensitivity when actual data are taken from target local portions. Thus, even if measurements are taken at local portions which are significantly removed from the center of the specimen 2, the results of analysis can be as precise as those for a local portion near or at the center.

The input unit 12 can be used to specify the positions of a plurality of local portions at different positions. In this manner, distributions of probability for finding specified elements from one position of the specimen 2 to another can be obtained by the data processing unit 14 as mapping data, and such mapping data can be effectively displayed on the display unit 15. With such mapping data prepared and displayed, specimens which are inhomogeneous in composition or specimens with segregates can be easily analyzed.

As explained above, the screen 3 can be moved linearly corresponding to the rotation of the container 8 so as to be positioned properly with reference to a local portion to be analyzed. In other words, it is not necessary, as is the case with conventional spectrometers, to rearrange the setting of the specimen even when a local portion far removed from its center area is to be analyzed. Moreover, specimens which are of an unusual shape or deformed need not be subdivided into small parts in order to be effectively analyzed. It also goes without saying that average values can also be obtained for a relatively large local portion set at the center of the specimen 2 by rotating the container 8.

Figure 3:
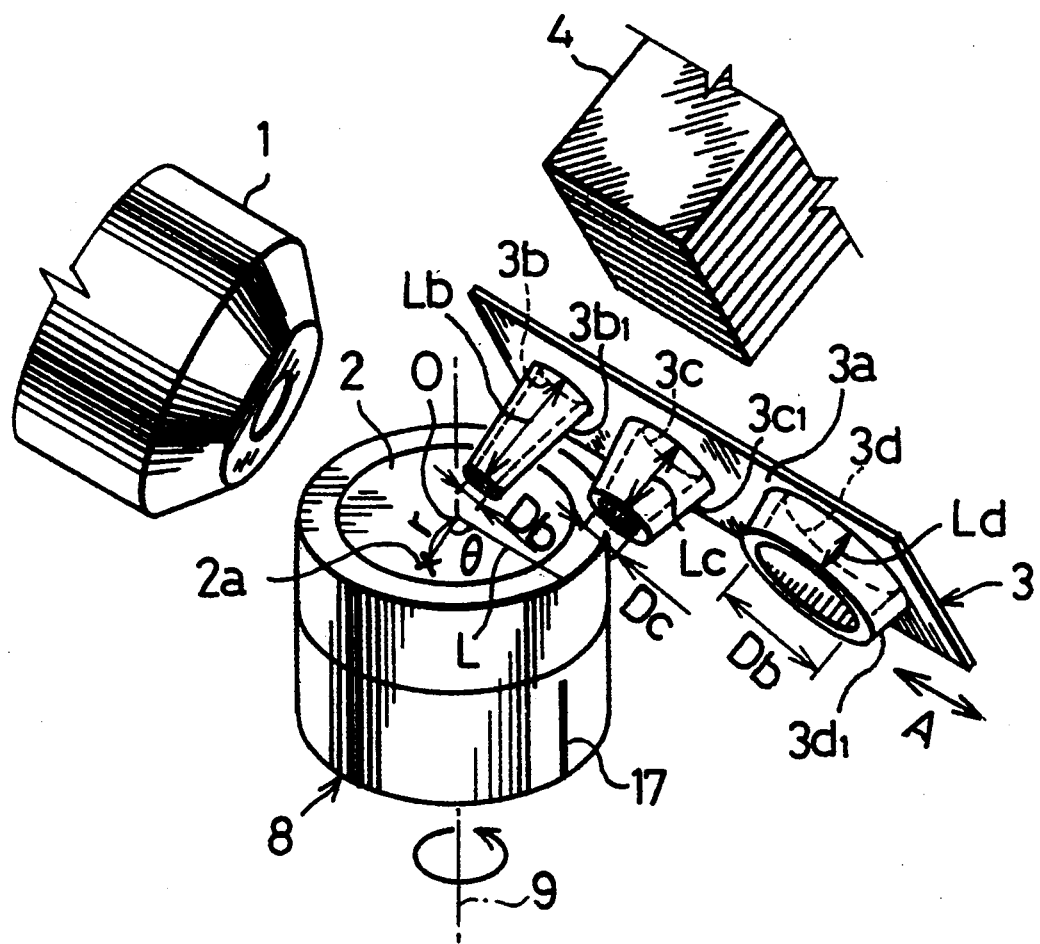
FIG. 3 is a perspective view of a portion of another X-ray fluorescence spectrometer according to a second embodiment of the invention with a specimen having a local portion with a relatively large exposed area with respect to the specimen container.

Another X-ray fluorescence spectrometer according to a second embodiment of the invention may be characterized, as shown in FIG. 3, as having a view-restricting screen 3 comprised not only of a flat plate 3a with a plurality of holes 3b, 3c and 3d but also of hollow (or tubular) frustoconical members 3b1, 3c1 and 3d1 mounted on the plate 3a around the individual holes 3b, 3c and 3d with their narrowed ends pointing in the direction of the specimen 2. These hollow (or tubular) members 3b1, 3c1 and 3d1 are formed such that the inner diameters of their hollow interiors become smaller towards their narrowed ends (or "tips") Db, Dc and Dd. The lengths of these members 3b1, 3c1 and 3d1 are indicated in FIG. 3 as Lb, Lc and Ld, respectively. The inner diameters of the interiors and the lengths Lb, Lc and Ld of the members 3b1, 3c1 and 3d1 are so determined with respect to one another such that only the area of a selected local portion can be "seen" from the side of the X-ray detector 7 through the screen 3 and that the irradiation of the selected local portion by the primary X-rays from the X-ray tube 1 will not be thereby interfered. In practice, therefore, if the hole 3b is the smallest and the hole 3d is the largest, the tips of the members 3b1 and 3d1 are the smallest and the largest, respectively, and the lengths Lb and Ld are respectively the largest and the smallest, as shown in FIG. 3.

Figure 4:
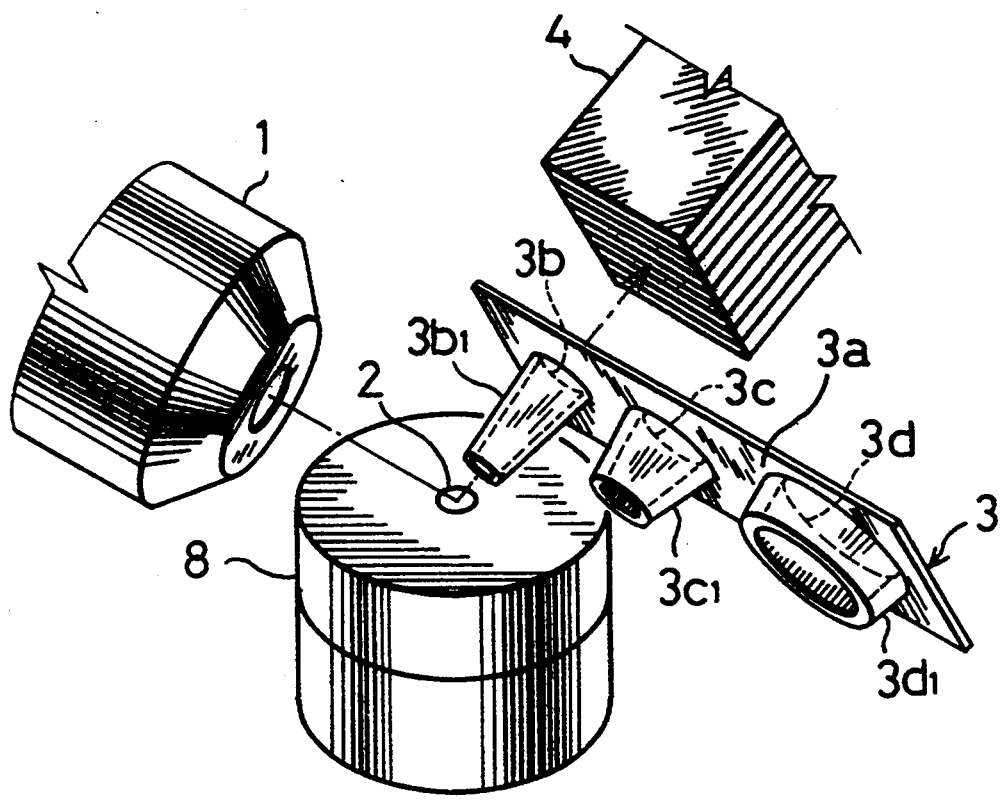
FIG. 4 is a perspective view of a portion of the spectrometer according to the second embodiment of the invention with a specimen having a local portion with a relatively small exposed area.
Figure 5:
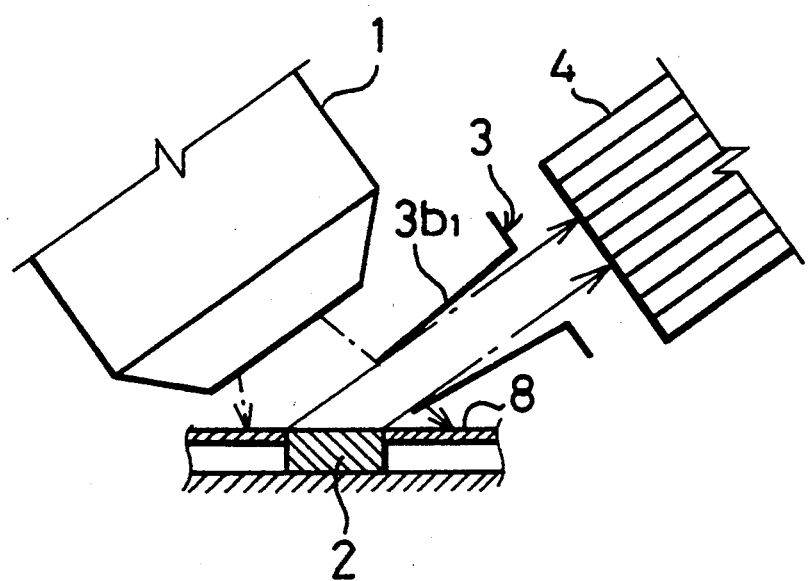
FIG. 5 is a sectional side elevation view of a portion of the spectrometer of FIG. 4.

In general, more precise analyses are possible with a spectrometer according to the second embodiment of the invention. In a case as shown in FIG. 4, where only a central portion of the specimen 2 is exposed with the other surface areas covered by a portion of the container 8, a suitable one of the members (3b1 in the example shown in FIG. 4) is selected according to the size of the exposed portion of the specimen 2 and brought opposite thereto by moving the plate 3a. Thus, as shown in FIG. 5 more clearly, the tip of the selected member 3b1 comes very close to the specimen 2 and hence only the exposed surface area can be "seen" through the hollow interior of the member 3b1 from the opposite side of the screen 3. Accordingly, unwanted fluorescent X-rays and scattered X-rays from the container 8 are shut off by the screen 8. The unwanted noise being thereby reduced for the analysis, the fluorescent X-rays generated from the specimen 2 can be introduced efficiently into the X-ray detector 7. The signal components contained in the detection output from the detector 7 becoming relatively larger, the signal-to-noise ratio (S/N) is improved for the analysis.

Figure 6:
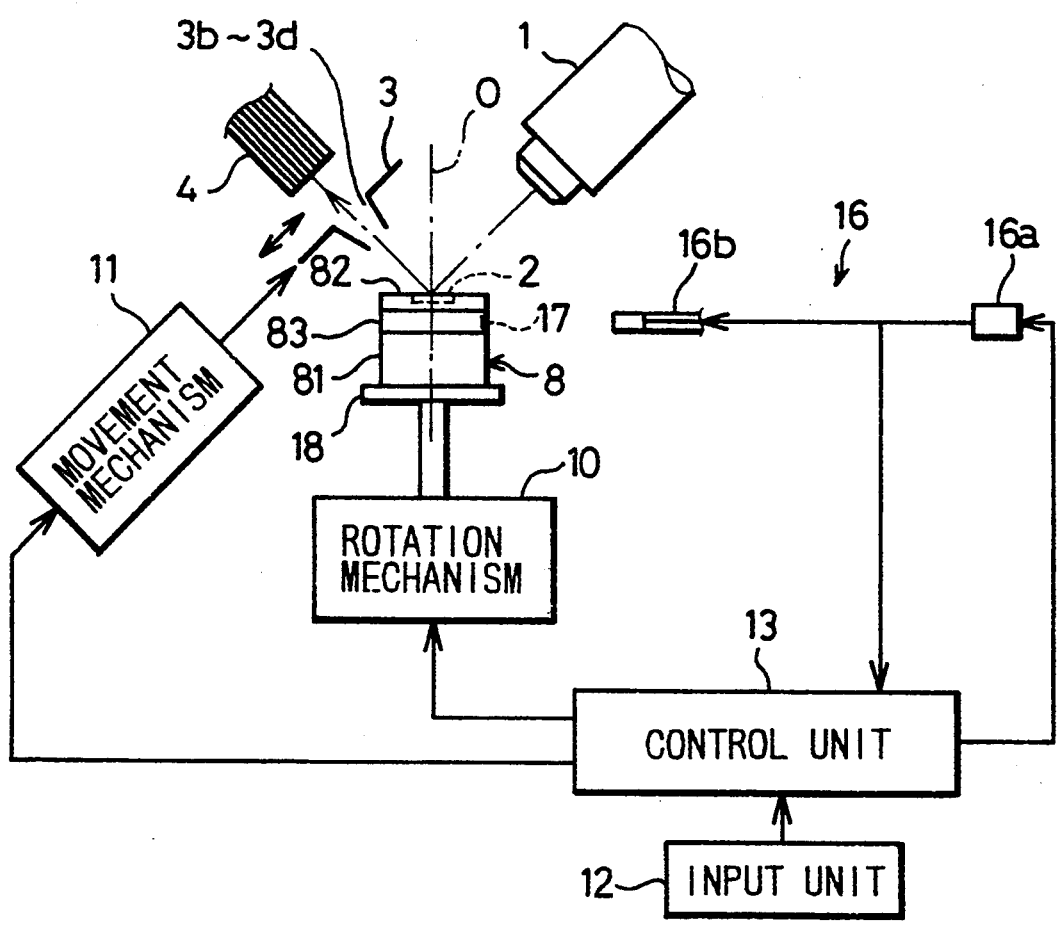
FIG. 6 is a schematic, in part in the form of a block diagram, of an X-ray fluorescence spectrometer according to a third embodiment of the invention.
Figure 7:
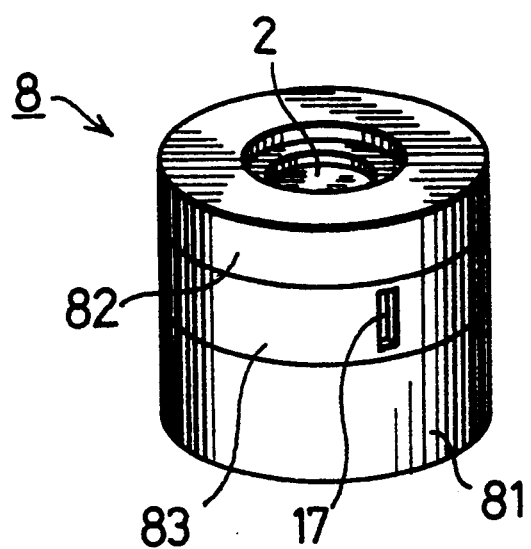
FIG. 7 is a perspective view of the specimen container shown in FIG. 6.
Figure 8:
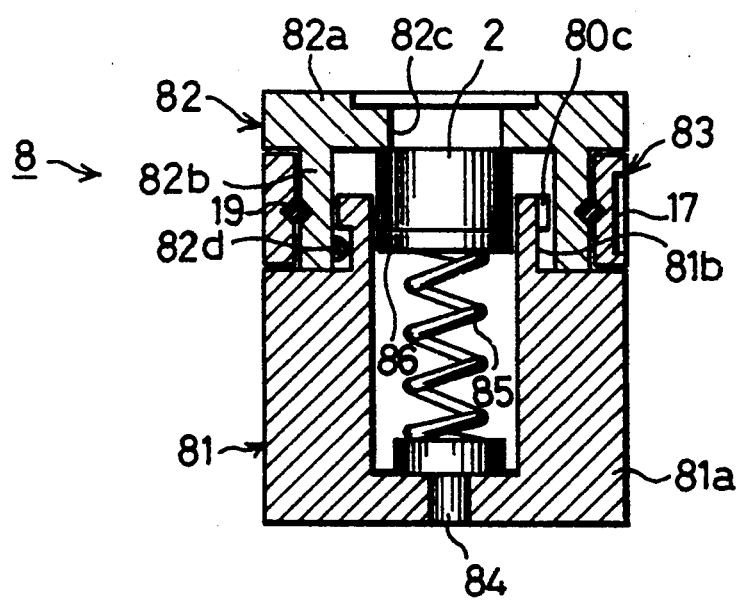
FIG. 8 is a vertical sectional view of the specimen container shown in FIG. 7.

Still another X-ray fluorescence spectrometer according to a third embodiment of the invention may be characterized, as shown in FIG. 6 (for which some of the components shown in FIG. 1 are omitted for clarity), as further comprising a mark-detecting unit 16 and controlling the rotation and movement mechanisms 10 and 11 on the basis of detection outputs therefrom as well as in response to data inputted through the input unit 12 such that selected holes in the screen 3 will be positioned opposite specified local portions to be analyzed. As shown in FIG. 6, the container 8 is mounted on a mounting table 18 and, as shown more clearly in FIGS. 7 and 8, the container 8 comprises a cylindrical container body 81, a lid 82 fitted at the top of the container body 81 and having a barrel portion, and a ring 83 fitted into this barrel portion of the lid 82. Clamped on the bottom of the container body 81 is a spring seat 84, on which a compressed spring 85 is positioned. A specimen seat 86 is attached on the upper end of the compressed spring 85. The upper portion of the container body 81 has a reduced diameter, and an annular groove 81b is formed around the upper peripheral surface of the container body 81 where the diameter is reduced. This annular groove is circumferentially cut at several points where engagement grooves 80c are formed for allowing engagement with the lid 82.

The lid 82 comprises a top portion 82a having a hole 82c at the center thereof and a barrel portion 82b. Protruding portions 82d are formed on the inner peripheral surface of the barrel portion 82b corresponding to the engagement grooves 80c for the lid 82. A ring 83 is rotatably fitted on the outer peripheral surface of the barrel portion 82b of the lid 82 through an O-ring 19.

A mark 17 for defining a reference angular position is formed on a circumferential area of the ring 83. The mark 17 is composed of a slit-like longitudinal groove formed by drilling a part of the ring 83 and coating its interior with black paint. The mark-detecting unit 16 for detecting the existence of the mark 17 is positioned opposite the outer peripheral surface of the ring 83.

The mark-detecting unit 16 comprises a light source 16a and an optical fiber 16b. The light from the light source 16a irradiates the outer peripheral surface of the ring 83 through the optical fiber 16b and is thereby reflected. The reflected light from the ring 83 is guided through the optical fiber 16b to the control unit 13. When the mark 17 faces the light-emitting end of the optical fiber 16b, the strength of the reflected light becomes smaller, and the mark-detecting unit 16 thereby detects the existence of the mark 17 and outputs a detection signal to the control unit 13.

When the specimen 2 is set in the container 8, it is first mounted on the specimen seat 86, and each of the protruding portions 82d is thereafter inserted into corresponding one of the grooves 80c on the upper portion of the container body 81.

Next, the lid 82 is rotated such that each of the protruding portions 82d is fitted into the annular groove 81b and the lid 82 is thus mounted on the container body 81, the specimen 2 being held between the specimen seat 86 and the top portion 82a of the lid 82.

Figure 9:
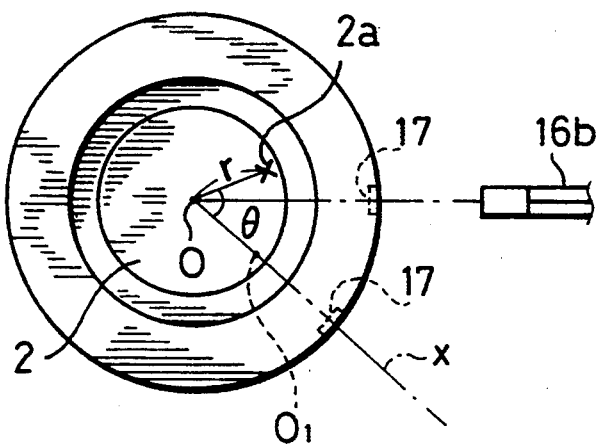
FIGS. 9(a) and 9(b) are plan views of a lid for the specimen container and an optical fiber of the mark-detecting unit shown in FIG. 6.
Figure 9:
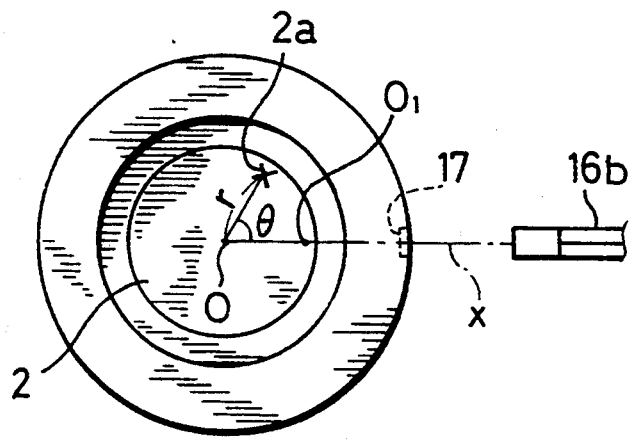

Procedures for local analysis are explained next with reference to FIG. 9. First, the center of rotation O of the specimen 2 and an angular reference point O1 serving as the reference points for measuring rotation are set and may be marked. The values of radial distance r between O and the local portion 2a to be analyzed and its angular position $\theta$ measured from the line x connecting the points O and O1 are inputted to the control unit 13 through the input unit 12. The setting of the specimen 2 to the container 8 is thus completed. Now, if the mark 17 is not on the reference line x, the ring 83 can be rotated such that the mark 17 comes to be on the reference line x.

Next, the container 8 is set on the table 18 such that the angular reference point O1, marked on the specimen 2, will come to coincide with the center of rotation O of the table 18. At this moment, the mark 17 may be at a position displaced from the light-emitting end of the optical fiber 16b as shown in FIG. 9(a).

When the input unit 12 is operated subsequently and a command to start a local analysis is given, the control unit 13 switches on the light source 16a and operates the pulse motor 10 to rotate the container 8 in the counterclockwise direction with reference to FIG. 9(a). When the mark 17 is thereby brought to a position opposite the light-emitting end of the optical fiber 16b as shown in FIG. 9(b), the intensity of the reflected light becomes reduced and this change in the intensity is detected by the control unit 13. At this moment, the reference line x agrees with the reference position recognized by the control unit 13 for controlling the rotation of the container 8. Accordingly, the control unit 13 sets this position of the mark 17 as the reference angle ($=0°$) for local analyses. After the container 8 is rotated clockwise, for example, by the inputted angle $\theta$ indicating the local portion 2a, the screen 3 is moved by the distance r by means of the movement mechanism 11. The hole 3b, 3c or 3d in the screen 3 can thus be brought opposite a pre-specified local portion 2a for local analysis.

The third embodiment of the invention was explained above for a situation where only one point on the specimen 2 is selected as a local portion, but many local portions can be selected on the specimen 2 by inputting values of r and $\theta$ for each of these portions. In other words, no extra efforts are required beyond what has been described above.

If the position of the mark 17 is fixed on the container 8, as was the case with the first and second embodiments of the invention, adjustments must be made initially to place the mark 17 on the reference line x when the specimen 2 is set in the container 8. With the third embodiment of the invention described above, however, the mark 17 can be easily moved and brought onto the reference line x by rotating the ring 83.

The third embodiment described above is advantageous also in that the reference position can be easily set for a local analysis and that mapping data are easily obtainable merely by specifying the positions to be analyzed.

Although the invention has been described above with reference to only a limited number of embodiments and examples, they are not intended to limit the scope of the invention. Many modifications and variations can be made within the scope of the invention. For example, the number of holes formed through the screen 3 need not be three, and the members 3b1, 3c1 and 3d1 formed therearound need not be frustoconical in shape. Although the ring 83 was shown above as being fitted around the outer surface of the lid 82, it may equally well be fitted into the container body 81. The mark 17 may be formed with a reflector mounted on the container 8. For the O-ring 19, a plate spring may be substituted.

The position of a local portion need not be expressed in the polar coordinates r and $\theta$. The control unit 13 may be so program to allow the input unit 12 to specify a position in any other suitable coordinate system and then convert the input data into the polar coordinate variables.

In the description given above, the smallest hole 3b through the screen 3 was placed opposite the target local portion 2a to be analyzed, but this is not to be interpreted as a limitation. Under different circumstances and/or for local portions of different sizes, the other holes 3b and 3d may be selected for the purpose of passing fluorescent X-rays.

In summary, all such modifications and variations that may be apparent to a person skilled in the art are intended to be within the scope of this invention.

What is claimed is:

1. An X-ray fluorescence spectrometer comprising:
   a container containing a specimen with a surface of said specimen exposed externally;
   screening means for restricting a field of view to a local portion of said specimen irradiated by X-rays from an X-ray tube;
   primary collimating means having an incident optical axis for collimating fluorescent X-rays from said specimen received through said screening means;
   rotating means for rotating said container around a predetermined axis of rotation;
   moving means for moving said screening means linearly perpendicular to said incident optical axis of said primary collimating means;

control means for controlling said moving means such that said screening means is moved to an adjacent position opposite said local portion;

input means for receiving position data indicative of the position of a local portion of said specimen to be analyzed; and control means for controlling said rotating means to rotate said container and said moving means to move said screening means according to said position data received by said input means.

2. The X-ray fluorescence spectrometer of claim 1 wherein said moving means moves said screening means linearly perpendicular to both said incident optical axis of said primary collimating means and to said axis of rotation.

3. The X-ray fluorescence spectrometer of claim 1 wherein said container has a mark thereon for indicating the angular position thereof;

said spectrometer further comprising mark-detecting means disposed near said container for detecting said mark;

said control means being adapted to operate said rotating means to rotate said container, to identify a reference angular position of said container by causing said detecting means to detect said mark, to further operate said rotating means to rotate said container from said reference angular position by an angle determined by said position data, and to operate said moving means to move said screening means linearly according to said position data.

4. The X-ray fluorescence spectrometer of claim 3 wherein said container includes a ring which is rotatably supported, said mark being attached to said ring.

5. The X-ray fluorescence spectrometer of claim 3 wherein said mark-detecting means includes a photosensor.

6. The X-ray fluorescence spectrometer of claim 3 wherein said mark-detecting means includes a light source and an optical fiber connected to said light source.

7. The X-ray fluorescence spectrometer of claim 1 wherein said screening means comprises a screening plate having one or more throughholes of different sizes.

8. The X-ray fluorescence spectrometer of claim 1 further comprising:

a dispersing means for dispersing fluorescent X-rays collimated by said primary collimating means;

a secondary collimating means for collimating fluorescent X-rays dispersed by said dispersing means;

an X-ray detector for detecting fluorescent X-rays collimated by said secondary collimating means; and data processing means for compensating for the effects on detection outputs from said X-ray detector due to the variations in the distance between local portions analyzed by said spectrometer and said axis of rotation.

9. The X-ray fluorescence spectrometer of claim 8 wherein said data processing means is programmed to store position data indicative of the effects on detection outputs from said X-ray detector due to the variations in the distance between local portions on a standard specimen and said axis of rotation and to use said position data to compensate for the effects on detection outputs from said X-ray detector due to the variations in the distance between local portions of interest and said axis of rotation.

* * * * *